US008246948B2

(12) United States Patent
Swain

(10) Patent No.: US 8,246,948 B2
(45) Date of Patent: *Aug. 21, 2012

(54) STIMULATION OF CARTILAGE FORMATION USING REDUCED PRESSURE TREATMENT

(75) Inventor: Larry D. Swain, San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/108,796

(22) Filed: May 16, 2011

(65) Prior Publication Data

US 2011/0218504 A1 Sep. 8, 2011

Related U.S. Application Data

(63) Continuation of application No. 12/491,445, filed on Jun. 25, 2009.

(60) Provisional application No. 61/076,028, filed on Jun. 26, 2008.

(51) Int. Cl.
A01N 3/00 (2006.01)
A61K 48/00 (2006.01)
A61F 2/00 (2006.01)

(52) U.S. Cl. .............. 424/93.7; 424/93.21; 424/426

(58) Field of Classification Search .............. 424/93.7, 424/93.21, 426
See application file for complete search history.

(56) References Cited

U.S. PATENT DOCUMENTS

| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |

(Continued)

FOREIGN PATENT DOCUMENTS

AU 550575 A1 8/1982

(Continued)

OTHER PUBLICATIONS

Sylvester et al. Arch Surg. 139:93-99, 2004.* International Search Report and Written Opinion date mailed May 6, 2010; PCT International Application No. PCT/US2009/048628.
International Search Report and Written Opinion date mailed Aug. 16, 2010; PCT International Application No. PCT/US2009/069031.
N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R 1986);pp. 94-96 copy and certified translation).
Louis C. Argenta, MD and Michael J. Morykwas, PhD; "Vacuum-Assisted Closure: A New Method for Wound Control and Treatment; Clinical Experience"; Annals of Plastic Surgery, vol. 38, No. 6, Jun. 1997; pp. 563-576.

(Continued)

Primary Examiner — Marcia S Noble
(74) Attorney, Agent, or Firm — SNR Denton US, LP

(57) ABSTRACT

A method of inducing new cartilage growth from periosteum in a mammal is provided. The method includes positioning a foam manifold in contact with the periosteum and positioning a drape over the foam manifold and the periosteum to create a sealed space between the drape and the periosteum. A reduced pressure is applied to the sealed space.

18 Claims, 3 Drawing Sheets

U.S. PATENT DOCUMENTS

| | | | |
|---|---|---|---|
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,053,050 A | 10/1991 | Itay |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A * | 6/1997 | Argenta et al. ............... 128/897 |
| 5,645,081 A | 7/1997 | Argenta et al. |
| 5,723,331 A | 3/1998 | Tubo et al. |
| 5,786,219 A | 7/1998 | Zhang et al. |
| 5,811,094 A | 9/1998 | Caplan et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,491,693 B1 | 12/2002 | Lytinas |
| 6,493,568 B1 | 12/2002 | Bell et al. |
| 6,553,998 B2 | 4/2003 | Heaton et al. |
| 6,695,823 B1 | 2/2004 | Lina et al. |
| 6,727,224 B1 | 4/2004 | Zhang et al. |
| 6,763,836 B2 | 7/2004 | Tasto et al. |
| 6,767,334 B1 | 7/2004 | Randolph |
| 6,814,079 B2 | 11/2004 | Heaton et al. |
| 6,840,962 B1 | 1/2005 | Vacanti et al. |
| 6,856,821 B2 | 2/2005 | Johnson |
| 6,936,037 B2 | 8/2005 | Bubb et al. |
| 6,949,525 B2 | 9/2005 | Hermida |
| 6,951,553 B2 | 10/2005 | Bubb et al. |
| 6,958,149 B2 | 10/2005 | Vukicevic et al. |
| 6,982,298 B2 | 1/2006 | Calabro et al. |
| 6,994,702 B1 | 2/2006 | Johnson |
| 7,004,915 B2 | 2/2006 | Boynton et al. |
| 7,070,584 B2 | 7/2006 | Johnson et al. |
| 7,077,832 B2 | 7/2006 | Fleischmann |
| 7,108,683 B2 | 9/2006 | Zamirowski |
| 7,169,151 B1 | 1/2007 | Lytinas |
| 7,186,224 B2 | 3/2007 | Windheuser |
| 7,214,202 B1 | 5/2007 | Vogel et al. |
| 7,279,612 B1 | 10/2007 | Heaton et al. |
| 7,316,672 B1 | 1/2008 | Hunt et al. |
| 7,346,945 B2 | 3/2008 | Phillips et al. |
| 7,351,250 B2 | 4/2008 | Zamierowski |
| 7,468,192 B2 | 12/2008 | Mizuno et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0225347 A1 | 12/2003 | Argenta et al. |
| 2004/0134502 A1 | 7/2004 | Mizuno et al. |
| 2004/0225296 A1 | 11/2004 | Reiss et al. |
| 2006/0036331 A1 | 2/2006 | Lu et al. |
| 2006/0154367 A1 | 7/2006 | Kihm et al. |
| 2007/0021697 A1 | 1/2007 | Ginther et al. |
| 2007/0021698 A1 | 1/2007 | Fleischmann |
| 2007/0123895 A1 | 5/2007 | Lytinas |
| 2007/0185426 A1 | 8/2007 | Ambrosio |
| 2008/0033324 A1 | 2/2008 | Cornet et al. |
| 2008/0269674 A1 | 10/2008 | Stone |
| 2008/0275409 A1 | 11/2008 | Kane et al. |
| 2009/0005796 A1 | 1/2009 | Swain |

FOREIGN PATENT DOCUMENTS

| | | |
|---|---|---|
| AU | 745271 | 4/1999 |
| AU | 755496 | 2/2002 |
| CA | 2005436 | 6/1990 |
| CA | 2216752 C | 7/2002 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| EP | 1466633 A1 | 10/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 98/46164 A1 | 10/1998 |
| WO | WO 98/53768 A1 | 12/1998 |
| WO | WO 99/13793 | 3/1999 |
| WO | WO 00/38755 | 7/2000 |
| WO | WO 00/59424 | 10/2000 |
| WO | WO 00/61206 | 10/2000 |
| WO | WO 03/018098 | 3/2003 |
| WO | WO 03/092620 | 11/2003 |
| WO | WO 2004/060148 | 7/2004 |
| WO | WO 2004/105576 | 12/2004 |
| WO | WO 2005/009488 | 2/2005 |
| WO | WO 2005/033273 | 4/2005 |
| WO | WO 2007/067685 | 6/2007 |
| WO | WO 2007/092397 | 8/2007 |
| WO | WO 2007/106589 | 9/2007 |
| WO | WO 2007/106590 | 9/2007 |
| WO | WO 2007/106591 | 9/2007 |
| WO | WO 2007/106592 | 9/2007 |
| WO | WO 2007/106594 | 9/2007 |
| WO | WO 2007/107330 | 9/2007 |
| WO | WO 2007/133555 | 11/2007 |
| WO | WO 2007/133556 | 11/2007 |
| WO | WO 2007/143060 | 12/2007 |
| WO | WO 2008/013896 | 1/2008 |
| WO | WO 2008/036162 | 3/2008 |
| WO | WO 2008/036359 | 3/2008 |
| WO | WO 2008/036361 | 3/2008 |
| WO | WO 2008/042481 | 4/2008 |
| WO | WO 2009/006226 A | 1/2009 |

OTHER PUBLICATIONS

Susan Mendez-Eastmen, RN; "When Wounds Won't Heal" RN Jan. 1996, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressing"; Letter to the Editor, British Journal of Plastic Surgery, 1998, vol. 51

(3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al., "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al., "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al., "Medical Textiles: Application of an Absorbable Barbed Bi-directional Surgical Suture"; Journal of Textile and Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al., "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al., "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al., "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, Managing Draining Wounds and Fistulae: "New and Established Methods," *Chronic Wound Care*, edited by D. Krasner (Health Management Publications, Inc., King of Prussia, PA 1990), pp. 240-246.

G. Živadinović, V. Đukić, Maksimović, Đ. Radak, and P. Peška, "Vacuum Therapy in the Treatment of Peripheral Blood Vessels," *Timok Medical Journal* 11 (1986), pp. 161-164 (copy and certified translation).

F.E Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).

M. Schein, R. Saadia J.R. Jamieson, and G.A.G Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R 1988) ("Solovev Abstract"), pp. 1-23.

V.A.C.® Therapy Clinical Guidelines: A Reference Source for Clinicians (Jul. 2007), pp. 1-88.

Restriction Requirement date mailed Aug. 12, 2011 for U.S. Appl. No. 12/491,445.

Response filed Sep. 8, 2011 for U.S. Appl. No. 12/491,445.

Gould and Auchincloss. Immunology Today 20(2):77-82, 1999.

Azimzadeh et al. Hematology and Cell Therapy 38(4):331-343, 1997.

\* cited by examiner

STIMULATION OF CARTILAGE FORMATION USING REDUCED PRESSURE TREATMENT

CROSS-REFERENCE TO RELATED APPLICATIONS

This application is a continuation of U.S. patent application Ser. No. 12/491,445, filed Jun. 25, 2009, which claims the benefit of U.S. Provisional Application No. 61/076,028, filed Jun. 26, 2008, all of which are hereby incorporated by reference.

BACKGROUND OF THE INVENTION

1. Field of the Invention

The present invention relates generally to tissue treatment systems and in particular to methods for stimulating cartilage formation.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifolding device. Unless otherwise indicated, as used herein, "or" does not require mutual exclusivity. The porous pad, often an open-cell foam, contains cells or pores that are capable of distributing reduced pressure to the tissue and channeling fluids that are drawn from the tissue. The porous pad is generally sized to fit the existing wound, placed in contact with the wound, and then periodically replaced with smaller pieces of foam as the wound begins to heal and becomes smaller. The porous pad often is incorporated into a dressing having other components that facilitate treatment. While reduced pressure therapy has been used to treat soft tissue injuries, it has not been used to promote, for example, cartilage regeneration.

Damage to cartilage through age, injury, wear and metabolic disorders, such as osteoarthritis, affect millions of people throughout the world. Indeed, it is currently believed that 85% of all Americans will develop degenerative joint disease as a result of normal activities that damage cartilage. The gradual degeneration and destruction of articular cartilage may be due to trauma, structural deformation of the joints and being overweight. The process thins the cartilage, in part through programmed cell death, or apoptosis. The clinical manifestations of cartilage damage or wear are often painful and debilitating, including swelling of the joint, crepitation, and decrease in functional mobility. As the condition worsens, pain may even limit minimum physical efforts and persist at rest making it difficult to sleep. If the condition persists without correction and/or therapy, the joint can be totally destroyed, leading the patient to major replacement surgery with a total prosthesis, or to disability. The complications of cartilage injury are multifold. For example, injured cartilage tends to cause additional damage to articulations and the articular surfaces. Damage to articular surfaces is linked to bone spur development, which further limits joint movement.

Moreover, cartilage is the main structural support of various parts of the body, such as ears and the nose. As such, a lack of cartilage from injury may also result in a cosmetic defect. Thus, in sum, damaged and degraded cartilage results in a reduced quality of life.

The body, however, cannot completely repair the cartilage. Cartilage is primarily composed of collagen fibers, proteoglycans and elastin fibers that form an extracellular matrix. The matrix is formed by specialized cells called chondrocytes. Chondrocytes are one of the few cell types that can survive with a minimal blood supply. However, when cartilage is damaged, the lack of an adequate blood supply to the chondrocytes results in an inability to regenerate new chondrocytes, a process that requires an increased amount of nutrients and access through the blood stream to other cells and proteins. Full thickness articular cartilage damage or osteochondral lesions may allow for normal inflammatory response, but then result in repair with functionally inferior fibrocartilage formation.

Current techniques to inhibit or delay degeneration of joint cartilage include use of anti-inflammatory agents, chondrogenic stimulating factors, antirheumatics, systemics, viscoprotection and injection of depot steroids. Other methods include implantation of chondrocytes or synthetic matrices. One method of treatment for cartilage damage is surgical intervention, with reattachment and reconstruction of the damaged tissue. None of the above methods are totally satisfactory, and those methods rarely restore full function or return the tissue to its native normal state. In addition, none, of those methods are proven to regenerate cartilage in situ and in vivo.

Further, there is no proven way to promote healing of dense connective tissue structures such as ligaments and tendons. Ligament and tendon injuries are commonplace and difficult to heal. Indeed, it is not uncommon to repair complete ruptures or tears of a ligament or tendon by immediate surgery to remove the damaged tissue and replace it with a graft. Post surgery, a graft recipient has to experience the long task of rehabilitation and healing. It is often difficult to repair ligaments and tendons by current methods. Thus, when repair is an option, the joints and muscles attached to the ligament or tendon are often immobilized to enable the tissue to heal.

As such, there is currently an acute need for a safe, simple, rapid, inexpensive and efficient system and method for regenerating connective tissues in areas where the connective tissue is missing, damaged, or worn.

SUMMARY

The problems presented by existing cartilage repair treatment regimens are solved by the systems and methods presented by the illustrative embodiments described herein. In one embodiment, a method of inducing new cartilage growth from periosteum includes positioning a foam manifold in contact with the periosteum. The method further includes positioning a drape over the foam manifold and the periosteum to create a sealed space between the drape and the periosteum. A reduced pressure is applied to the sealed space.

In another embodiment, a method of stimulating cartilage formation at a tissue site having periosteum is provided. The method includes applying a foam manifold to the periosteum and applying reduced pressure to the foam manifold and the tissue site for a time sufficient to cause new cartilage formation at the tissue site.

In still another embodiment, a system for stimulating cartilage formation at a tissue site includes a foam manifold positioned in contact with periosteum at the tissue site. A drape is positioned over the foam manifold and the tissue site to create a sealed space between the drape and the tissue site. A reduced pressure source is in fluid communication with the sealed space.

Other objects, features, and advantages of the illustrative embodiments will become apparent with reference to the drawings and detailed description that follow.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to the location of a wound or defect on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Figure 1:
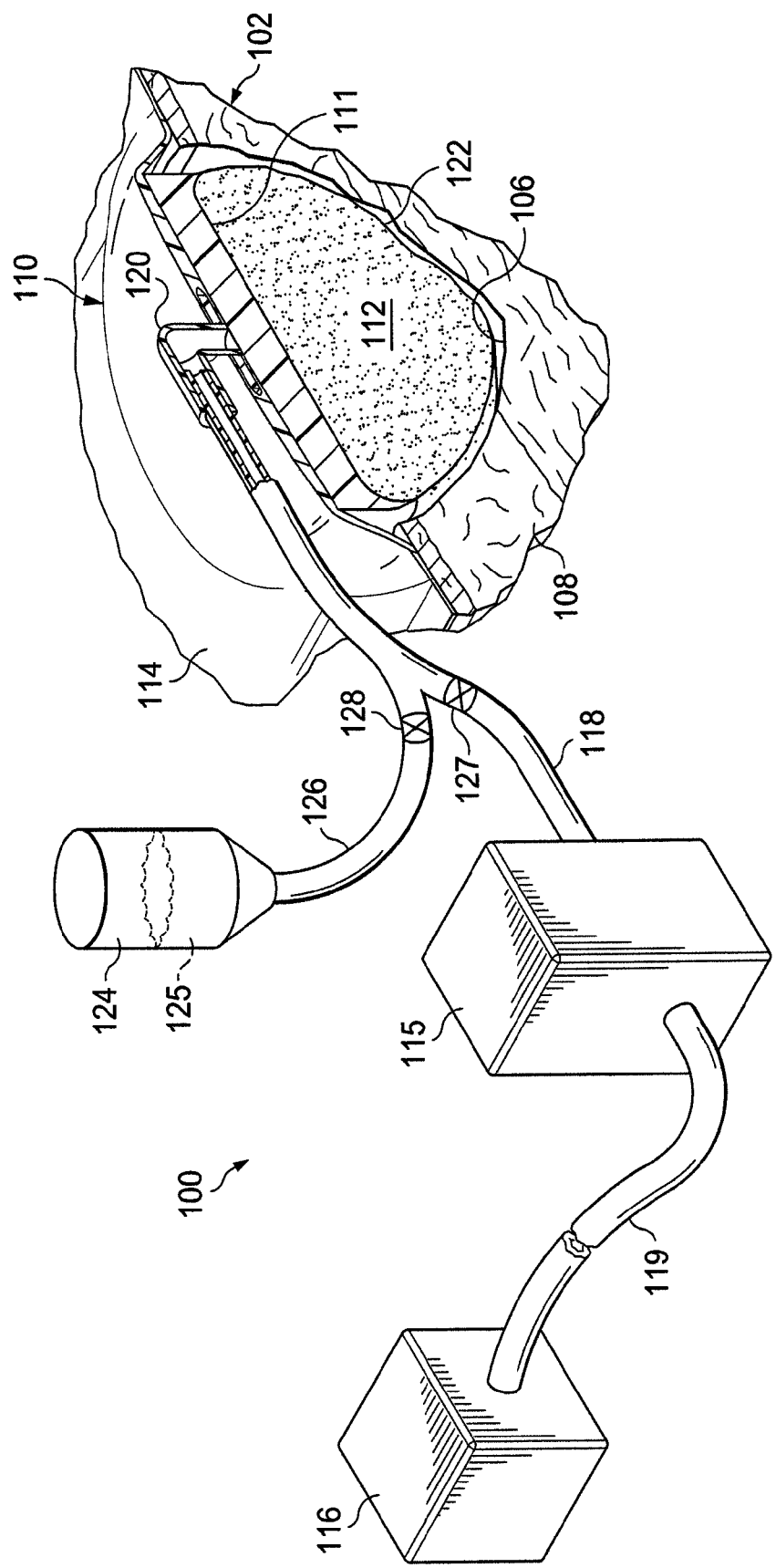
FIG. 1 is an illustrative embodiment of a reduced-pressure therapy system for treating tissue.

Referring to FIG. 1, an illustrative embodiment of a system 100 for applying reduced-pressure therapy to a tissue site 102 is shown. The illustrative embodiments of the system 100 apply reduced-pressure therapy to a wound 106 at the tissue site 102 which includes, for example, cartilage that needs to be repaired by regeneration. It should be understood that the tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. Treatment of tissue site 102 may include removal of fluids, e.g., ascites or exudate, delivery of fluids, e.g., saline or materials such as growth factors, and delivery of reduced pressure, for facilitating the growth of cartilage. The cartilage wound 106 on the tissue site 102 may be due a variety of causes, including trauma, surgery, wear, arthritis, cancer, etc., or may be congenital.

The system 100 comprises a reduced pressure dressing 110, which includes a manifold 111 adapted to distribute the reduced pressure to the tissue site 102 and a scaffold 112 adapted for placement adjacent the wound 106, and a drape 114 at least partially covering the reduced pressure dressing 110 to provide a seal covering the wound 106 at the tissue site 102. A chondrocyte or chondrocyte precursor can be placed directly on the tissue site 102 or be contained within a scaffold 112 that is applied to the tissue site 102. The system 100 further comprises a canister 115 with a filter (not shown) and a reduced pressure source 116, wherein the canister 115 is in fluid communication with the reduced pressure dressing 110 via a conduit 118 and is also in fluid communication with the reduced pressure source 116 via a conduit 119. The reduced pressure source 116 is adapted to supply reduced pressure to the manifold 111 and the scaffold 112 which distribute the reduced pressure to the tissue site 102 when in operation. The conduit 118 may fluidly communicate with the reduced pressure dressing 110 through a tubing adapter 120 to provide the reduced pressure through the drape 114 to the manifold 111.

In yet another embodiment, the reduced pressure dressing 110 may be constructed from multiple layers or materials in addition to or in lieu of the manifold 111, the scaffold 112, and the drape 114. Some of these layers may be bioabsorbable while others are not. For instance, the manifold 111 may include a bioabsorbable material adjacent to a bio-inert material or a bioabsorbable material that degrades more slowly (as the terms are defined below), such that the reduced pressure dressing 110 may be removed and replaced without removal of any absorbable scaffold 112, that supports tissue growth, from the wound 106.

The canister 115 may be a fluid reservoir, or collection member, to filter and hold exudates and other fluids removed from the tissue site 102. The canister 115 may include other devices (not shown) including the following non-limiting examples: a pressure-feedback device, a volume detection system, a blood detection system, an infection detection system, a flow monitoring system, and a temperature monitoring system. Some of these devices may be formed integral with the reduce-pressure source 116. For example, a reduced-pressure port on the reduced-pressure source 116 may include a filter member that includes one or more filters, e.g., an odor filter.

The reduced-pressure source 116 may be any device for supplying a reduced pressure, such as a vacuum pump, wall suction, or other source. While the amount and nature of reduced pressure applied to a tissue site will typically vary according to the application, the reduced pressure will typically be between −5 mm Hg and −500 mm Hg and more typically between −100 mm Hg and −300 mm Hg. The particular protocol used in reduced pressure treatment depends upon the location of the tissue site 102, the reduced pressure dressing 110, or pharmacological agents being utilized. Additionally, reduced pressure may be a substantially continuous or cyclical application such that it oscillates the pressure over time. The reduced pressure source 116 may include sensors, processing units, alarm indicators, memory, databases, software, display units, and user interfaces that further facilitate the application of reduced pressure treatment to the tissue site 102. In one example, a sensor or switch (not shown) may be disposed at or near the reduced pressure source 116 to determine a source pressure generated by the reduced pressure source 116. The sensor may communicate with a processing unit that monitors and controls the reduced pressure but is delivered by the reduced pressure source 116.

The cartilage may be any type of cartilage. For example, hyaline cartilage is the most common type of cartilage in the body and characteristically contains collagen type II fibers in its extracellular matrix. Hyaline cartilage is found in articular joints, costal cartilage (ribs), nose, larynx, and growth plate. Another type of cartilage is elastic cartilage found in ear, trachea and epiglottis. The third type of cartilaginous tissue, fibrocartilage, is present in the pubic symphysis, intervertebral disc, parts of the articular joints, menisci and in sites connecting tendons or ligaments to bones. There also exist various combinations or intermediates of these types of cartilage, such as the epiphyseal cartilage in the growth or cartilage plate.

The manifold 111 of the reduced pressure dressing 110 is adapted to contact the scaffold 112 or portions of the tissue site 102. The manifold 111 may be partially or fully in contact with the tissue site 102 being treated by the reduced pressure dressing 110. When the tissue site 102 is a wound, the manifold 111 may partially or fully fill the wound. The manifold 111 may be any size, shape, or thickness depending on a variety of factors, such as a type of treatment being implemented or the nature and size of the tissue site 102. For example, the size and shape of the manifold 111 may be customized by a user to cover a particular portion of the scaffold 112 and/or the tissue site 102. The manifold 111 may have, for example, a square shape, or may be shaped as a circle, polygon, an irregular shape, or any other shape. In one illustrative embodiment, the manifold 111 is a foam material that distributes reduced pressure to the scaffold 112 and the tissue site 102 when the manifold 111 is in contact with, or near, the scaffold 112. Foam material may be either hydrophobic or hydrophilic. In one non-limiting example, the manifold 111 is an open-cell, articulated polyurethane foam such as GranuFoam® dressing available from Kinetic Concepts, Inc. of San Antonio, Tex.

In some embodiments, the manifold 111 is made from a hydrophilic material, where the manifold 111 functions to wick fluid away from the tissue site 102, while continuing to provide reduced pressure to the scaffold 112 and the tissue site 102 as a manifold. Without being bound by any particular mechanism, the wicking properties of the manifold 111 can draw fluid away from the scaffold 112 and the tissue site 102 by capillary flow or other wicking mechanisms. An example of hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Additional foams that may exhibit hydrophilic characteristics include hydrophobic foams that have been treated or were coated to provide hydrophilicity.

In another embodiment, the manifold 111 is constructed from a bioabsorbable material, natural or synthetic, that does not have to be removed from the tissue site 102 following use of the reduced pressure dressing 110. Bioabsorbable material is material that is capable of being absorbed in the body or removed from the body by excretion or metabolic functions; prior to absorption, the bioabsorbable material may be chemically, enzymatically, or otherwise degraded in vivo into simpler chemical species. Suitable bioresorbable materials may include, without limitation, a polymeric blend of polylactic acid (PLA) and polyglycolic acid (PGA). The polymeric blend may also include without limitation polycarbonates, polyfumarates, and caprolactones. The manifold 111 may further serve as a scaffold for new cell growth, or may be used in conjunction with the scaffold 112 to promote cell-growth.

The manifold 111 may further promote granulation at the tissue site 102 as reduced pressure is applied through the reduced pressure dressing 110. For example, any or all of the surfaces of the manifold 111 may have an uneven, course, or jaded profile that causes microstrains and stresses at the scaffold 112 and the tissue site 102 when reduced pressure is applied through the manifold 111. These microstrains and stresses have been shown to increase new tissue growth.

The scaffold 112 may be placed adjacent to, in contact with, or substantially over the tissue site 102 to promote the growth of the cartilage in the wound 106. As indicated above, the scaffold 112 may also function as a manifold when transferring reduced pressure to the tissue site 102. The scaffold 112 is a three-dimensional porous structure that provides a template for cell growth of the cartilage 108 within the wound 106. Nonlimiting examples of scaffold materials include calcium phosphate, collagen, PLA/PGA, hydroxyapatite, carbonates, and processed allograft materials. The scaffold 112 may also assist in delivering fluids to, or removing fluids from, the tissue site 102. The scaffold 112 may further comprise a distribution surface 122 that is positioned adjacent to the wound 106 to facilitate fluid flow, chondrocyte migration, and the like for moving a fluid and other material to or from the tissue site 102 to the pores in the scaffold 112. In some embodiments, the scaffold 112 is flexible to conform to the shape or contour of the wound 106 at the tissue site 102. The design of the scaffold 112 may also serve to prevent cartilage overgrowth. The shape and flexibility of the scaffold 112 may be selected without undue experimentation depending on the type of cartilage being treated in the location of the cartilage in the body treated.

A chondrocyte or chondrocyte precursor may be grafted, or otherwise applied, to the tissue site 102 or the scaffold 112 to facilitate the growth of the cartilage 108. An example of a chondrocyte precursor is a mesenchymal stem cell. The source of the chondrocyte or chondrocyte precursor may be an osteochondral graft, autologous to the patient, or comprising allograft, xenograft, or artificially prepared tissue. In one embodiment, the tissue source may be chondrocytic cell cultures, such as chondrocyte or stem cell cultures which have been prepared through ex vivo cell culture methods, with or without additional growth factors. For examples of cell culture methods, see, e.g., U.S. Pat. Nos. 5,226,914; 5,811,094; 5,053,050; 5,486,359; 5,786,217 and 5,723,331. The tissue may also be harvested by traditional non-cell culture based means, using techniques such as mosaicplasty, in which cartilage is harvested using commercially available instruments such as Acufex7, COR System, or Arthrex7 Osteochondral Autograft Transfer System. Further, the tissue harvested may be applied directly to the scaffold 112, or may be cultured beforehand.

The cells, chondrocyte, or chondrocyte precursor may be transfected, either transiently or stably, to further comprise a recombinant nucleic acid. Non-limiting examples of such nucleic acids include those that encode a protein, such as a cytokine, an enzyme, or a regulatory protein; a regulatory nucleic acid such as a promoter that causes a native protein to be overexpressed or silenced (e.g., to inhibit cancer initiation or growth); an miRNA or another RNAi molecule; an antisense molecule; a marker to assist in monitoring tissue formation; etc. The skilled artisan can determine and prepare, without undue experimentation, a chondrocyte or chondrocyte precursor comprising an appropriate recombinant nucleic acid for any particular application.

Other cells may also be seeded onto the scaffold 112 and/or placed on or into the tissue site 102 to stimulate the growth of cartilage. Non-limiting examples include fibroblasts, immune cells, stem cells that are not a chondrocyte precursor, etc. In some embodiments, attachment of the cells to the scaffold 112 may be enhanced by coating the scaffold 112 with compounds such as basement membrane components, agar, agarose, gelatin, gum arabic, collagen types I, II, III, IV, and V, fibronectin, laminin, glycosaminoglycans, polyvinyl alcohol, mixtures thereof, and other hydrophilic and peptide attachment materials known to those skilled in the art of cell culture. In another embodiment, the cells are seeded onto the scaffold 112, and the scaffold 112 is incubated before the scaffold 112 is applied to the tissue site 102.

A cytokine may be applied to the tissue site 102 or in the scaffold 112 as indicated above. As used herein, a cytokine is a protein that affects cellular growth, proliferation or differentiation, including growth factors and hormones. In some embodiments, the cytokine is one that can encourage cartilage growth. Nonlimiting examples include bone morphogenic protein (BMP)-2, BMP-6, BMP-7, transforming growth factor-β (TGF-β), insulin-like growth factor (IGF), platelet-derived growth factor (PDGF), or cartilage-derived retinoic acid sensitive protein (CD-RAP). The cytokine may be synthetic or naturally produced, or produced naturally or transgenically by cells placed at the tissue site 102 or in the scaffold 112.

The scaffold 112 may include, without limitation, calcium phosphate, collagen, PLA/PGA, hydroxyapatite, carbonates, and/or processed allograft materials. In another embodiment, the scaffold 112 may be used to release at least one therapeutic or prophylactic agent to the tissue site 102 by binding at least one therapeutic or prophylactic agent to the surface of the scaffold 112. For example, an antibiotic may also be applied to the scaffold 112, which is then released to the tissue site 102.

In some embodiments, the scaffold 112 is a porous material that includes a plurality of open chambers or "pores" that are connected by flow channels to allow fluid communication between the pores. The size, shape, or interconnectivity of the pores may be uniform, random, or patterned, and may be altered to enhance or control cartilage formation, response, repair, or host integration. Further, the size, shape, or interconnectivity of the pores in the scaffold 112 may be altered to enhance or control the integration of newly formed cartilage 108 with surrounding healthy tissue at the tissue site 102. In various embodiments, the scaffold 112 has a high void-fraction (i.e., a high content of air). It is desired in some embodiments that the pores are designed to allow the attachment of infiltrating cells to induce new cartilage formation. As explained above, the pores and flow chambers may be seeded with chondrocytes or other cell types in advance to promote cartilage formation. The flow channels in the scaffold 112 also facilitate distribution of fluids provided to and removed from the tissue site 102, including the transfer of reduced pressure to the tissue site 102.

In one embodiment, the scaffold 112 is made primarily of an open pore material that includes a plurality of pores fluidly connected to adjacent pores, where a plurality of flow channels is formed by and between the open pores of the material. The variations in size and shape of the pores results in variations in flow channels and can be used to alter flow characteristics of fluid through the material. In some embodiments, the scaffold 112 pore size ranges between 25 µm and 500 µm. In other embodiments, the pore size is between 50 µm and 250 µm. In additional embodiments, the pore size is between 50 µm and 150 µm.

The scaffold 112 may be formed of any biocompatible material, i.e. a material that does not elicit any undesirable local or systemic effects in vivo. A biocompatible scaffold 112 should also have the mechanical and biochemical properties that provide adequate support for tissue growth and cell proliferation. The materials can be characterized with respect to mechanical properties such as tensile strength using an Instron tester, molecular weight by gel permeation chromatography (GPC), glass transition temperature by differential scanning calorimetry (DSC) and bond structure by infrared (IR) spectroscopy. The material may also be characterized with respect to toxicology by, for example, mutagen tests, e.g. involving an Ames assay or an in vitro teratogenicity assay, or biochemical, cell, or implantation studies in animals for immunogenicity, inflammation, release or degradation.

In one embodiment, the scaffold 112 is formed of a bio-inert material, i.e., a material that does not elicit any response in vivo and does not bioabsorb or otherwise degrade in vivo. In another embodiment, the scaffold 112 is formed of a bioabsorbable material as that term in defined above. Regardless of whether the scaffold 112 is bioabsorbable or bio-inert when it contacts the tissue site 102, the scaffold 112 may also be biocompatible. If the scaffold 112 is made of bioabsorbable materials, the materials may be designed to degrade within a desired time frame. In one embodiment, the desired degradation time frame is six to twelve weeks. In another embodiment, the desired degradation time frame is between three months and one year. In yet another embodiment, the desired degradation time is greater than a year. Further, in some embodiments, scaffolds 112 made of bioabsorbable materials may degrade in a manner related to the molecular weights of the materials used to make the scaffold 112. In those embodiments, scaffolds 112 comprising a higher molecular weight material often retain structural integrity for longer periods of time than scaffolds 112 comprising lower molecular weight materials.

The scaffold 112 may be formed by melt-spinning, extrusion, casting, or other techniques well known in the polymer processing area. Preferred solvents, if used, are those which are removed by the processing or which are biocompatible in the amounts remaining after processing. Examples of polymers which can be used to form scaffolds 112 include natural and synthetic polymers. Synthetic polymers that may be used include, but are not limited to, bioabsorbable polymers such as polylactic acid (PLA), polyglycolic acid (PGA), polylactic-coglycolide acid (PLGA), and other polyhydroxyacids, polycaprolactones, polycarbonates, polyamides, polyanhydrides, polyamino acids, polyortho esters, polyacetals, degradable polycyanoacrylates and degradable polyurethanes, as well as a polylactide-coglycolide (PLAGA) polymer or a polyethylene glycol-PLAGA copolymer. Examples of natural polymers include, but are not limited to, proteins such as albumin, collagen, fibrin, and synthetic polyamino acids, and polysaccharides such as alginate, heparin, and other naturally occurring biodegradable polymers of sugar units. The polymeric blend may also include without limitation polycarbonates, polyfumarates, and capralactones.

In some embodiments, the bioabsorbable scaffold 112 is made of PLA, PGA or PLA/PGA copolymers. PLA polymers may be prepared from the cyclic esters of lactic acids. Both L (+) and D (−) forms of lactic acid can be used to prepare the PLA polymers, as well as the optically inactive DL-lactic acid mixture of D (−) and L (+) lactic acids. PGA is the homopolymer of glycolic acid (hydroxyacetic acid). Typically, in the conversion of glycolic acid to polyglycolic acid, glycolic acid is initially reacted with itself to form the cyclic ester glycolide, which in the presence of heat and a catalyst is converted to a high molecular weight linear-chain polymer. It is also contemplated that the scaffold 112 may be felted mats, liquids, gels, foams, or any other biocompatible material that provides fluid communication through a plurality of channels in three dimensions.

The drape 114 covers the reduced pressure dressing 110 and serves as a semi-permeable barrier to transmission of fluids such as liquids, air, and other gases. The drape 114, which in some embodiments provides structural support for the reduced pressure dressing 110, may be coupled to the reduced pressure dressing 110 or the manifold 111 using any technique, including via an adhesive. As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. Specific non-limiting examples of the techniques by which the manifold 111 may be coupled to the drape 114 include welding (e.g., ultrasonic or RF welding), bonding, adhesives, cements, etc. In alternative embodiments, the drape 114 is not a separate, attached structure, but instead the manifold 111 itself may include a lining of impermeable materials that functions the same as the drape 114.

The drape may be any material that provides a pneumatic or fluid seal. The drape may, for example, be an impermeable or semi-permeable elastomeric material. "Elastomeric" means having the properties of an elastomer. It generally refers to a polymeric material that has rubber-like properties. More specifically, most elastomers have elongation rates greater than 100% and a significant amount of resilience. The resilience of a material refers to the material's ability to recover from an elastic deformation. Nonlimiting examples of elastomers include natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Specific examples of drape materials include a silicone drape, 3M Tegaderm® drape, acrylic drape such as one available from Avery Dennison, or an incise drape.

In operation, the system 100 is used to stimulate formation of cartilage at the tissue site 102. A caretaker can apply a chondrocyte or chondrocyte precursor to the tissue site 102 or the reduced pressure dressing 110, and then apply reduced pressure to the tissue site 102 via the manifold 111 and the scaffold 112 for a time sufficient to cause new cartilage formation at the tissue site 102. The application of reduced pressure can result in the flexible drape 114 compressing and conforming to the surface of the tissue site 102 as air is removed from within the space between the drape 114 and the tissue site 102. In some applications, the system 100 may be used to cosmetically alter tissue having cartilage, such as a nose or ear. Cartilage may also be harvested on one mammal and then transplanted to another mammal, e.g., growing a nose or ear on a mouse for transplantation to a human. The system 100 may also be applied to a cartilage wound 106 and used to at least partially fill the wound 106.

The system 100 may also allow effective control of fixation, temperature, pressure (and its associated gradients for vital gases such as oxygen), osmotic forces, oncotic forces, and the addition or removal of various nutrients and pharmacological agents. Still further, the devices to apply reduced pressure in the current system and methodology may be enabled to transfer elements for the manipulation of gas and liquid pathways by preprogrammed, coordinated influx and efflux cycles. Such cycles would be designed to maintain the desired integrity and stability of the system while still allowing variations in multiple forces, flows, and concentrations within tolerated ranges.

The system 100 may also be configured to deliver fluid, liquids or gas, to the tissue site 102. In this embodiment, a fluid supply 124 for delivering a fluid 125 to the tissue site 102 fluidly communicates with the reduced pressure dressing 110 by a conduit 126 that may be connected directly to the reduced pressure dressing 110 (not shown) or indirectly via the conduit 118 which requires the use of valves 127 and 128 for controlling the delivery of reduced pressure from the reduced pressure source 116 and/or fluid 125 from the fluid supply 124, respectively. The fluid supply 124 may be separate from, attached to, or integrated within the reduced-pressure source 116. The fluid supply 124 enables treatment procedures to infuse the tissue site 102 with fluids to flush contaminants, counter infection, or promote tissue growth in the wound 106. Thus, the fluid supply 124 can be used to deliver various irrigation fluids, growth factors, antibiotics, anesthetics, antibacterial agents, antiviral agents, cell-growth promotion agents, or chemically active agents to the tissue site 102. The fluid supply 124 can also be used to deliver gaseous fluids to the tissue site 102 for a similar purpose including, for example, the delivery of sterile air in small quantities to promote and maintain the therapeutic effect at the tissue site 102 with or without the reduced pressure being maintained.

Figure 2:
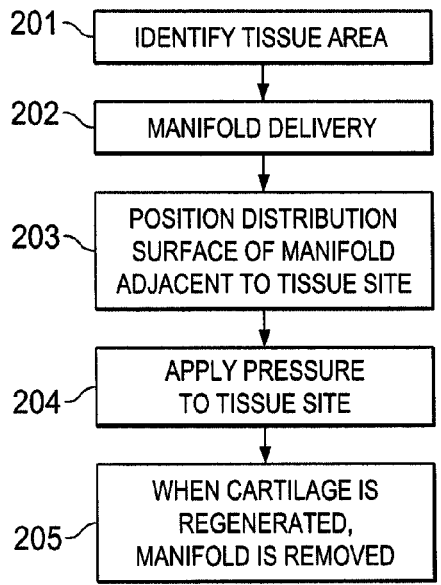
FIG. 2 is a flow chart illustrating a method of administering a reduced pressure therapy to a tissue site requiring cartilage regeneration according to an illustrative embodiment.

Referring to FIG. 2, a flow chart is provided outlining an illustrative embodiment of a method of administering reduced-pressure therapy to a tissue site requiring cartilage regeneration or healing by use of the reduced pressure system. First, the tissue area of interest is identified, for example, by a caretaker (step 201). If the tissue site is located underneath the skin of a patient, i.e., not in direct line of sight, the caretaker may identify the tissue site by use of imaging equipment and techniques, such as MRI imaging. At this time, the caretaker would then determine the best path through the patient's body to reach the tissue area which would cause the least damage to healthy, normal tissues.

The manifold is then delivered to the tissue site (step 202). Further, depending upon the embodiment, conduits to deliver reduced pressure, fluids, gases, or air may be connected before or after the manifold is delivered to the tissue site. If the tissue site is located underneath the skin of the patient, the manifold may be delivered to the tissue site by insertion into the body through the skin of the patient and through any interstitial tissue.

In some embodiments, it is contemplated that the tissue site has insufficient space to insert a manifold. In these embodiments, a device may be inserted that creates a void. For example, this device may be an inflatable device. Once a void is prepared, the manifold may then be delivered.

The main distribution surface of the manifold is then positioned adjacent to the tissue site (step 203). A reduced pressure is then applied to the tissue site (step 204). The reduced pressure may be applied continuously or in an intermittent fashion. Further, it is contemplated that the reduced pressure may be alternated with delivery of fluids, air, or agents that promote healing or regeneration as previously discussed.

The length and force of the reduced-pressure therapy may depend upon various factors determined appropriate by a caretaker, such as previous experience, connective tissue regeneration rate, and the like. The manifold may be removed upon partial or complete regeneration of the cartilage (step 205).

Figure 3:
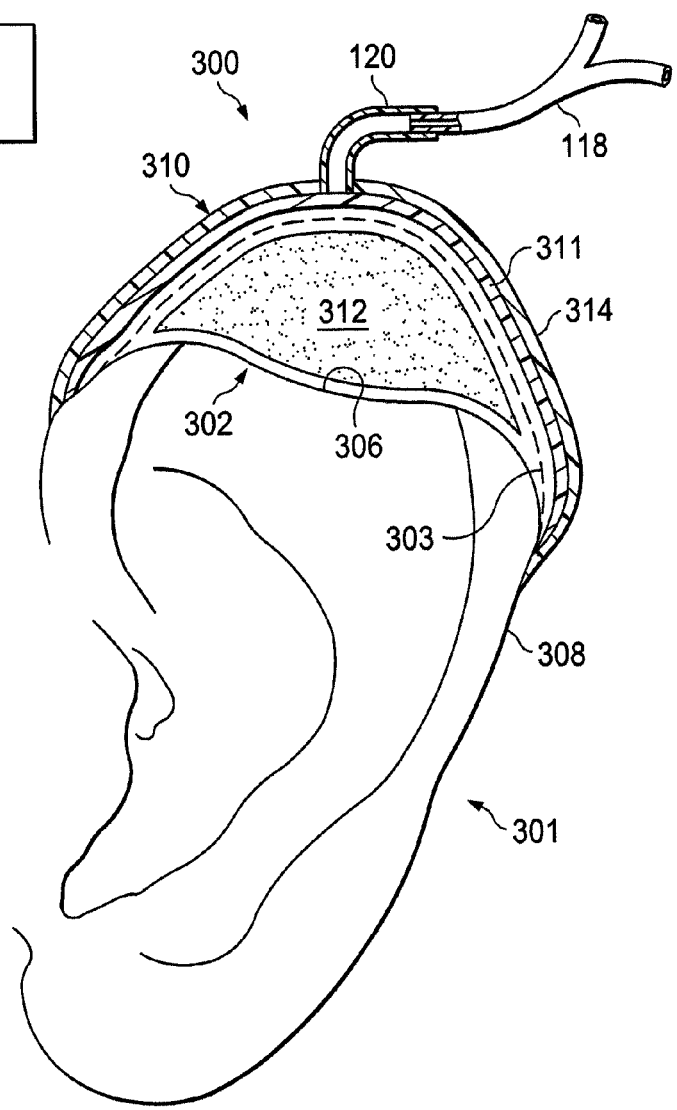
FIG. 3 illustrates use of a mold to facilitate administration of reduced pressure therapy to induce connective tissue regeneration according to an illustrative embodiment.

In some embodiments, the open pores or flow channels of the scaffold may be designed to promote a certain connective tissue growth in a particular three-dimensional shape. Thus, in one embodiment, the scaffold may be designed to promote cartilage growth on the surface of the body such as, for example, an ear. Referring more specifically to FIG. 3, an illustrative embodiment of a system 300 for applying reduced-pressure therapy to an ear 301 at a tissue site 302 on the top of the ear 301 is shown. This illustrative embodiment of the system 300 applies reduced-pressure therapy to a missing section of the ear 301, or cartilage wound 306, to regenerate the missing cartilage. The cartilage wound 306 of the tissue site 302 may have been due to any cause including, for example, trauma, surgery, or cancer. The system 300 comprises a reduced pressure dressing 303 which includes a manifold 311 adapted to distribute the reduced pressure to the tissue site 302 and a scaffold 312 adapted for placement adjacent the cartilage wound 306, and a drape 314 at least partially covering the reduced pressure dressing 303 to provide an airtight seal covering the cartilage wound 306 at the tissue site 302. The remaining components of the system 300 include the same components comprising the system 100 described above including, for example, the tube adapter 120 fluidly coupling the conduit 118 to the reduced pressure dressing 303. All the components of the system 300 described above operate in a fashion similar to the components of the system 100.

As indicated above, the scaffold 312 may be placed adjacent to, in contact with, or substantially over the tissue site 302 to promote the growth of the cartilage in the cartilage wound 306. The scaffold 312 is a three-dimensional porous structure that provides a template for cell growth of the cartilage within the wound 306. The shape and flexibility of the scaffold 312 may be selected based on the desired shape of the ear 301 as indicated by the dashed line on the reduced pressure dressing 303. In one embodiment, a mold (not shown) may be used to form the scaffold 312 into the desired shape. Once the mold is created to fit the ear 301 at the tissue site 302 with the missing portion, it can be used to form the scaffold 312 into the three-dimensional shape desired to repair the cartilage wound 306. As indicated above, the scaffold 312 may contain chondrocytes or a coping may be applied directly to the cartilage wound 306. When the reduced pressure dressing 303 including the scaffold 312 is positioned within the void of the cartilage wound 306, the drape 314 is positioned to cover the reduced pressure dressing 303 as described in detail above. Reduced pressure therapy can then be applied by use of the reduced-pressure source (not shown) via the conduits 118 fluidly coupled to the reduced pressure dressing 303.

In another embodiment, the mold may be positioned over the cartilage wound 306 creating a void that may be filled with a fluid containing chondrocytes that is delivered by a fluid supply (not shown) via the conduit 118 or other independent supply of fluid. After the fluid fills the void between the mold and the cartilage wound 306, the fluid hardens to form the three-dimensional scaffold 312 that assumes the desired shape for the regenerated cartilage at the tissue site 302. The scaffold may also be seeded with chondrocytes after hardening.

Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the example. An illustrative embodiment is described in the following example.

EXAMPLE

Induction of Cartilage Tissue Formation

Cartilage formation was observed in response to the application of reduced pressure therapy to the surface of intact cranial periosteal membranes. These observations are of significance in that cartilage formation in response to a therapy is unique and of great interest in the field of tissue engineering. These formations were observed in the absence of scaffold materials and only with the application of reduced pressure. No cartilage formation was observed in controls not subjected to reduced pressure.

Cartilage degeneration caused by congenital abnormalities or disease and trauma is of great clinical consequence. Because of the lack of blood supply and subsequent wound-healing response, damage to cartilage generally results in an incomplete repair by the body. Full-thickness articular cartilage damage, or osteochondral lesions, allow for the normal inflammatory response, but result in inferior fibrocartilage formation. Surgical intervention is often the only option. Treatments for repair of cartilage damage are often less than satisfactory, and rarely restore full function or return the tissue to its native normal state. This Example demonstrates the induction of new cartilage from periosteum using GranuFoam® and reduced pressure treatment.

A foam manifold and reduced pressure were evaluated for their ability to induce the periosteum to synthesize new cartilage. The intact, undamaged crania of rabbits were exposed. A GranuFoam® (KCI Licensing, Inc., San Antonio Tex.) foam dressing was applied to the bone. With some treatments, the foam-covered bone was also subjected to reduced pressure. After treatment, the treated bone was subjected to paraffin embedding, sectioning, and staining to evaluate the effect of the treatment on new bone formation.

Figure 4A:
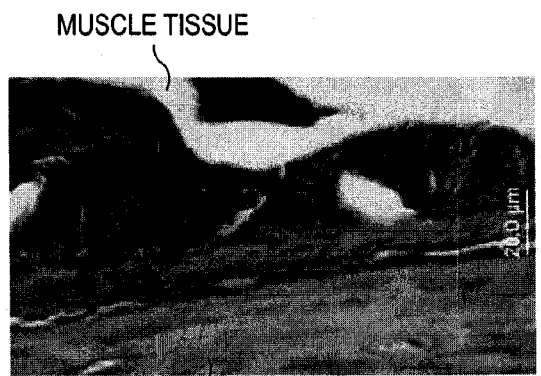
FIGS. 4A-4C illustrate histological sections demonstrating the results of reduced pressure therapy for cartilage regeneration according to an illustrative embodiment.
Figure 4B:
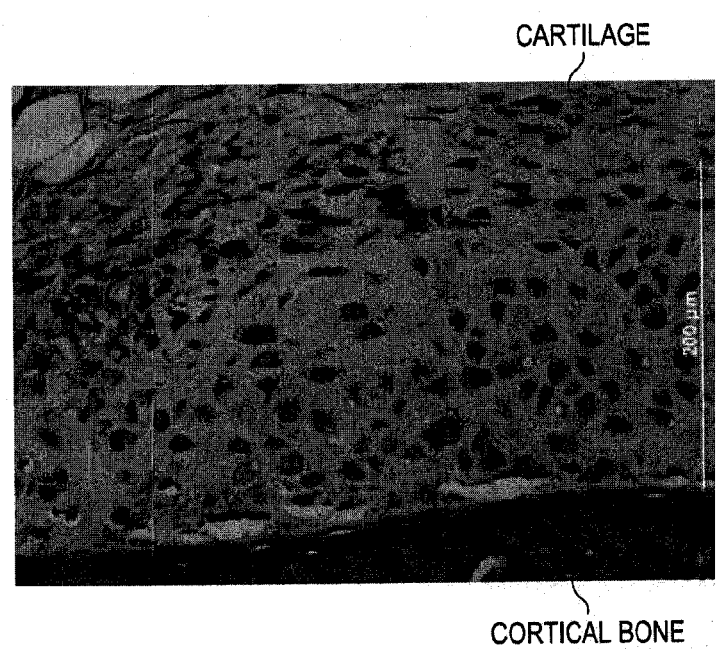
Figure 4C:
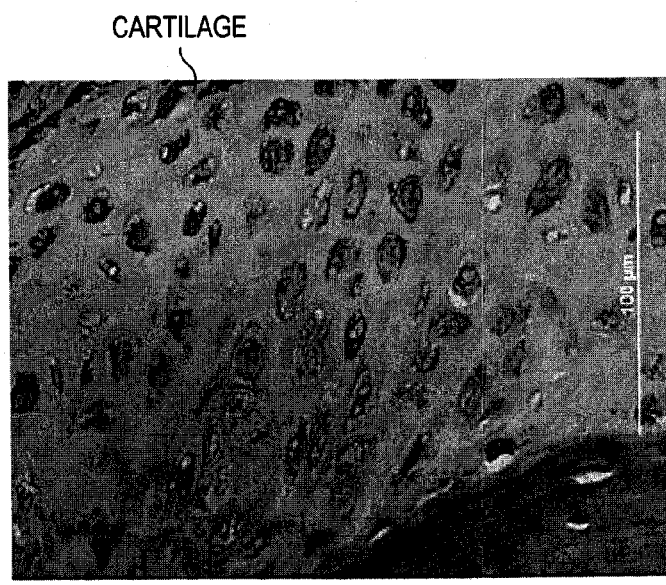

FIG. 4A shows a naïve, undamaged periosteum in rabbit cranium. The dots denote the demarcation between the cortical bone and the thin layer of the periosteum. By contrast, FIGS. 4B and 4C show that, with the use of GranuFoam® and reduced pressure (−125 mm Hg), extensive cartilage tissues was induced overlying the periosteum.

In view of the above, it will be seen that the several advantages of the invention are achieved and other advantages attained. As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of inducing new cartilage growth from periosteum in a mammal, the method comprising positioning a biocompatible foam manifold in contact with the periosteum; positioning a drape over the biocompatible foam manifold and the periosteum to create a sealed space between the drape and the periosteum; and applying reduced air pressure to the sealed space, thereby inducing new cartilage growth from the periosteum.

2. The method of claim 1, wherein the new cartilage growth overlies the periosteum.

3. The method of claim 1, wherein the periosteum is intact and undamaged.

4. The method of claim 1, wherein the reduced air pressure is applied to the sealed space by a reduced air pressure source.

5. The method of claim 1 further comprising: applying a chondrocyte or mesenchymal stem cell (MSC) to the periosteum by applying said chondrocyte or said MSC to the biocompatible foam manifold.

6. The method of claim 1, wherein the foam manifold serves as a scaffold for cartilage growth and is comprised of a biocompatible material.

7. The method of claim 6, wherein the biocompatible material comprises a polyhydroxy acid, a poly(caprolactone), a polycarbonate, a polyamide, a polyanhydride, a polyamino acid, a polyortho ester, a polyacetal, a degradable polycyanoacrylate or a degradable polyurethane.

8. The method of claim 6, wherein the biocompatible material comprises a polylactide-coglycolide (PLAGA) polymer or a polyethylene glycol-PLAGA copolymer.

9. The method of claim 1, wherein the foam manifold serves as a scaffold for cartilage growth and is comprised of a bioabsorbable material.

10. A method of stimulating cartilage formation at a tissue site having periosteum, the method comprising: applying a biocompatible foam manifold to the periosteum such that the biocompatible foam manifold is in contact with the periosteum; and applying reduced air pressure to the biocompatible foam manifold and the tissue site for a time sufficient to cause new cartilage formation at the tissue site.

11. The method of claim 10, wherein the new cartilage overlies the periosteum.

12. The method of claim 10, wherein the periosteum is intact and undamaged.

13. The method of claim 10, wherein the reduced air pressure is applied to the foam manifold and the tissue site by a reduced air pressure source.

14. The method of claim 10, further comprising: applying a chondrocyte or MSC to the periosteum by applying said chondrocyte or said MSC to the biocompatible foam manifold.

15. The method of claim 10, wherein the foam manifold serves as a scaffold for cartilage growth and is comprised of a biocompatible material.

16. The method of claim 15, wherein the biocompatible material comprises a polyhydroxy acid, a poly(caprolactone), a polycarbonate, a polyamide, a polyanhydride, a polyamino acid, a polyortho ester, a polyacetal, a degradable polycyanoacrylate or a degradable polyurethane.

17. The method of claim 15, wherein the biocompatible material comprises a polylactide-coglycolide (PLAGA) polymer or a polyethylene glycol-PLAGA copolymer.

18. The method of claim 10, wherein the foam manifold serves as a scaffold for cartilage growth and is comprised of a bioabsorbable material.

* * * * *